(12) United States Patent
Dawson et al.

(10) Patent No.: US 11,833,359 B2
(45) Date of Patent: Dec. 5, 2023

(54) BULKHEAD ANCHOR FOR MEDICAL DEVICE LEADS

(71) Applicant: Advanced Neuromodulation Systems, Inc., Plano, TX (US)

(72) Inventors: Chris Dawson, Cambridge (GB); Adam Jackson, Cambridge (GB); Aaron Raines, Dallas, TX (US); Manasi Reardon, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 17/228,238

(22) Filed: Apr. 12, 2021

(65) Prior Publication Data

US 2022/0161040 A1  May 26, 2022

Related U.S. Application Data

(60) Provisional application No. 63/117,771, filed on Nov. 24, 2020.

(51) Int. Cl.
*A61N 1/05* (2006.01)
*A61N 1/375* (2006.01)

(52) U.S. Cl.
CPC ......... *A61N 1/37518* (2017.08); *A61N 1/057* (2013.01); *A61N 1/0558* (2013.01); *A61N 2001/0582* (2013.01)

(58) Field of Classification Search
CPC .. A61N 1/37518; A61N 1/0558; A61N 1/057; A61N 2001/0582
See application file for complete search history.

(56) References Cited

U.S. PATENT DOCUMENTS

| 4,672,979 | A | * | 6/1987 | Pohndorf | ............... | A61N 1/375 |
| | | | | | | 607/126 |
| 5,843,146 | A | * | 12/1998 | Cross, Jr. | ............. | A61N 1/0558 |
| | | | | | | 607/117 |

(Continued)

FOREIGN PATENT DOCUMENTS

RU    2639337 C1    12/2017

OTHER PUBLICATIONS

Patent Cooperation Treaty, International Search Report and Written Opinion issue for PCT Application No. PCT/US2021/060555, dated Mar. 1, 2022, 13 pages.

*Primary Examiner* — Eugene T Wu
(74) *Attorney, Agent, or Firm* — Norton Rose Fulbright US LLP (57) ABSTRACT

Systems and methods which provide a bulkhead anchor configuration in which an anchor body includes flexure finger members and a radial bulkhead operable in cooperation to impart a radial compressive force to a corresponding lead body are described. A first portion of a bulkhead anchor body may comprise a plurality of flexure finger members disposed in a corolla configuration forming an anchor lumen through which a lead body may be inserted. A second portion of the bulkhead anchor body may comprise a radial bulkhead having a flexure profile configured to operatively engage the flexure finger members. A locking mechanism may be used to retain the first and second portions of the bulkhead anchor in their relative positions such that the radial compressive force is maintained upon the lead body indefinitely.

40 Claims, 5 Drawing Sheets

(56) References Cited

U.S. PATENT DOCUMENTS

| | | | |
|---|---|---|---|
| 5,957,968 A | 9/1999 | Belden et al. | |
| 8,140,172 B1 | 3/2012 | Jones et al. | |
| 8,301,268 B1 | 10/2012 | Jones et al. | |
| 8,494,652 B2 | 7/2013 | Cantlon et al. | |
| 9,026,227 B2 | 5/2015 | Daglow | |
| 9,433,756 B2 | 9/2016 | Oster | |
| 2006/0127158 A1* | 6/2006 | Olson | A61N 1/0558 401/53 |
| 2007/0078399 A1 | 4/2007 | Olson | |
| 2011/0238040 A1 | 9/2011 | Johnson et al. | |
| 2012/0221109 A1* | 8/2012 | Malinowski | A61B 90/11 623/17.19 |
| 2013/0204336 A1* | 8/2013 | Sharma | A61N 1/0558 607/117 |
| 2015/0012076 A1 | 1/2015 | Jones | |
| 2018/0093094 A1 | 4/2018 | Wolf, II | |
| 2019/0209225 A1 | 7/2019 | Songer et al. | |

\* cited by examiner

BULKHEAD ANCHOR FOR MEDICAL DEVICE LEADS

CROSS-REFERENCE TO RELATED APPLICATIONS

The present application claims the benefit of U.S. Provisional Patent Application No. 63/117,771, entitled "BULKHEAD ANCHOR FOR MEDICAL DEVICE LEADS," filed Nov. 24, 2020 the disclosure of which is hereby incorporated by reference herein in its entirety as if fully set forth below and for all applicable purposes.

TECHNICAL FIELD

The present invention relates to medical device leads and, more particularly, to anchors for leads used in the medical field.

BACKGROUND OF THE INVENTION

Implantable medical devices are used for a wide variety of medical conditions. For example, a number of implantable medical devices have been commercially distributed that allow various medical agents to be controllably infused after implantation of the respective device within a patient. Such implantable medical devices may be used for the infusion of insulin, opiates, antispasmodic drugs, intrahepatic chemotherapy agents, and other therapeutic agents in a number of countries subject to the regulatory requirements of those countries. As another example, a number of implantable medical devices have been commercially distributed that allow electrical pulses or signals to be controllably delivered to a targeted tissue or nerves after implantation of the respective device within a patient. Such implantable medical devices may be used for cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression.

Implantable infusion devices typically include a central housing that includes a reservoir to hold the infusate, a septum to allow infusate to be introduced into the reservoir, an energy source to drive the infusate from the reservoir and through an outlet port, and various flow control elements. The central housing portion of the device is typically implanted in a suitable subcutaneous region with the septum positioned immediately below the skin of the patient to facilitate access to the reservoir for refilling purposes. To deliver the infusate from the reservoir, a lead in the form of a catheter is usually attached to the outlet port of the central housing to receive the infusate outflow. The distal end of the catheter is implanted within the patient adjacent to the appropriate therapy site (e.g., at a suitable intrathecal location to allow introduction of an infusate directly into the spinal fluid of the patient).

Implantable electrical stimulation devices generally include an implanted pulse generator that generates electrical pulses or signals that are transmitted to a targeted tissue or nerves through a therapy delivery element, such as a lead with electrodes. Controlled placement of the therapy delivery element is required for improved therapeutic efficacy or reduced side effects. Retaining the implanted therapy delivery element in the desired location also creates difficulties because the location may change over time as the patient moves.

Whether in a stimulation, sensing or element delivery capacity, leads (e.g., catheter or lead having electrodes) are commonly implanted along peripheral nerves, within the epidural or intrathecal space of the spinal column, and around the heart, brain, or other organs or tissue of a patient. For example, leads are often inserted such that the lead ends are adjusted precisely within the area of placement so as to maintain an orientation, position, spacing, etc. with respect to surrounding tissue to facilitate effective treatment of one or more indications. Current lead designs, however, are often prone to movement (e.g., axially, radially and/or longitudinally) after insertion if steps are not taken to control such movement. Typically, some mechanism is employed to anchor the leads so that the therapeutic agent (e.g., infusate or electrical signal) will continue to be delivered to the appropriate site. Accordingly, various forms of anchoring structures have been utilized to discourage movement of the lead and/or the electrodes, such as to facilitate satisfactorily long functional survival time of the lead, to avoid the reprogramming or replacement of the lead to restore effective therapy, etc.

Most anchor structures for use with implantable medical device leads are either slid over the lead or clamped over the lead. In some examples, the anchor structure is secured to the lead at the same time the anchor is sutured to the fascia. For example, an anchor may be slid onto the proximal end of a lead body while maintaining the position of the lead within the body of the patient. The anchor may be secured to the lead by tying ligatures around grooves in the anchor when the anchor is sutured to the fascia or other tissue (e.g., supraspinous ligament). Existing techniques for securing anchors to the lead body can be problematic. For example, the force needed to secure the anchor to the lead is usually more than the force needed to secure the anchor to the fascia, which can lead to the lead moving axially within the anchor.

Some anchor designs attempt to address the potential for the lead moving axially within the anchor by implementing a twist-lock technique. For example, the anchor may comprise two parts that, when slid over the lead and positioned where desired, may be twisted relative to each other to cause a cam mechanism to engage a compressive force upon the lead body. Such an interface may, however, provide non-uniform force around the periphery of the lead body where interfaced with the anchor. For example, the compressive force may be concentrated at a point corresponding to a cam engagement point. Such concentrated forces on the lead can be stress points that can result in damage to some configurations of leads.

Recently, leads for implantable electrical stimulation devices have begun to be configured for compatibility for use in situations where they may be exposed to a source of high-power radio frequency (RF) radiation. For example, a patient having an implanted neurostimulation device (e.g., a spinal cord stimulator (SCS)) providing spinal cord stimulation therapy may be subject to a diagnostic procedure in which magnetic resonance imaging (Mill) is used. A lead may be configured for shielding from the high-power RF radiation emitted by MRI scanning systems using a conductive material (e.g., tantalum braid) embedded within the outer sheath of the lead (e.g., within or surrounded by insulating material forming the lead body).

RF shielded lead configurations may not be particularly well suited for accommodating a compressive force concentrated at a particular point. For example, stress points introduced upon a lead body by an anchor may damage the braided shielding and/or polymer outer sheath of a lead. Such damage may manifest as the sheath material being scraped away to expose the braiding and/or the braiding deforming under the anchor clamping load.

BRIEF SUMMARY OF THE INVENTION

The present invention is directed to systems and methods which provide a bulkhead anchor configuration in which an anchor body includes flexure finger members and a radial bulkhead operable in cooperation to impart a radial compressive force to a corresponding lead body. For example, in accordance with some embodiments of the invention, a first portion of a bulkhead anchor body may comprise a plurality of flexure finger members disposed in a corolla configuration (e.g., a closed flower petal or crown-like arrangement) forming an inner diameter (e.g., anchor lumen) through which a lead body may be inserted. The flexure finger members of embodiments may comprise one or more features for aiding in gripping of the lead, may be over-molded in a material that increases the friction between lead and anchor, etc. A second portion of the bulkhead anchor body of embodiments may comprise a radial bulkhead having a flexure profile configured to operatively engage the flexure finger members. Once a bulkhead anchor of this configuration is disposed at a desired position axially along the lead body, the portion of the bulkhead anchor comprising the radial bulkhead may be manipulated to induce flexure of the flexure finger members and cause a radial compressive force to be imparted upon the lead body by the bulkhead anchor. A locking mechanism may be used to retain the first and second portions of the bulkhead anchor in their relative positions such that the radial compressive force is maintained upon the lead body indefinitely.

Aspects of a bulkhead anchor of embodiments of the invention may be variously configured, such as for the particular lead the anchor is to be used with, the area of the body the lead and/or anchor are to be deployed in, the use scenario of the lead to be anchored, etc. For example, bulkhead anchor configuration parameters, such as the number of flexure finger members used, the gripping features of the flexure finger members, contact length between the fingers and the lead, the compression between the fingers and the lead, may be selected so as to provide one or more desired operational aspects (e.g., provide a maximum or minimum compressive force, set the amount of pull out force required for axial displacement of the anchor on the lead, etc.).

Embodiments of bulkhead anchors are configured to reduce or eliminate damage to the leads while maintaining robust anchoring performance. For example, bulkhead anchors configured according to concepts of the present invention provide a tight friction interface between the anchor and the lead without introducing sharp concentrated shear forces on the lead that can be stress points. In operation of bulkhead anchors of embodiments, compressive forces are distributed substantially equally around the lead body, such as by the flexure finger members relatively uniformly squeezing the lead around a portion at which the anchor is disposed.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

DETAILED DESCRIPTION OF THE INVENTION

Bulkhead anchor configurations are provided according to embodiments of the invention for use in anchoring or otherwise discouraging movement of medical device leads. For example, a bulkhead anchor may be utilized with respect to a lead in the form of a catheter comprising part of an implantable medical device operable to deliver an infusate to a targeted tissue or treatment area. As another example, a bulkhead anchor may be utilized with respect to a lead in the form of an electrical lead comprising part of an implantable medical device operable to deliver electrical pulses or signals to a targeted tissue or nerves.

To aid in understanding concepts herein, the description that follows describes examples relating to implantable medical devices of a spinal cord stimulation (SCS) system. However, it is to be understood that, while embodiments of a bulkhead anchor are well suited for applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder subluxation, headache, etc.

A bulkhead anchor according to concepts herein may be utilized with one or more therapy delivery elements comprising an electrical lead including one or more electrodes to deliver electric pulses or signals to a respective target tissue site in a patient. Additionally or alternatively, a bulkhead anchor may be utilized with one or more therapy delivery elements comprising an electrical lead including sensing electrodes to sense physiological parameters (e.g., blood pressure, temperature, cardiac activity, etc.) at a target tissue site within a patient.

In accordance with some embodiments, a bulkhead anchor may be utilized with one or more therapy delivery elements comprising a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In the various embodiments contemplated by this disclosure, therapy may include stimulation therapy, sensing or monitoring of one or more physiological parameters, fluid delivery, and the like. A therapy delivery element (also referred to as a lead) may include pacing or defibrillation leads, stimulation leads, sensing leads, fluid delivery conduit, extensions for any of the above, or combinations thereof. A target tissue site may refer generally to the target site for implantation of a therapy delivery element, regardless of the type of therapy.

Figure 1A:
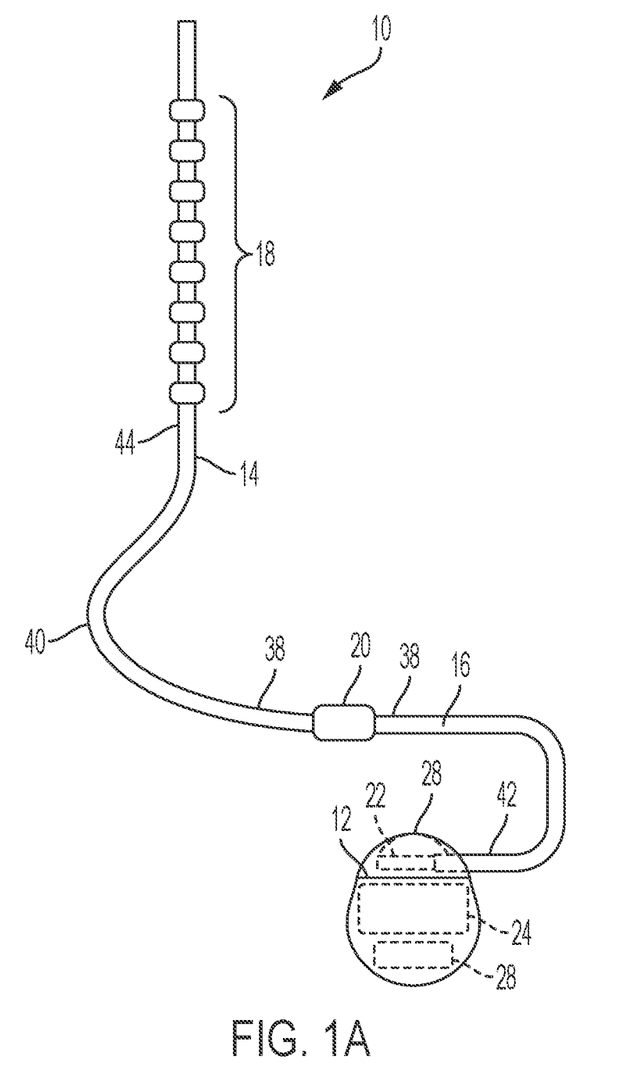
FIG. 1A shows a therapy delivery system as may utilize embodiments of a bulkhead anchor of the present invention.

FIG. 1A illustrates a generalized therapy delivery system 10 that may be used in SCS, as well as other stimulation applications. Therapy delivery system 10 generally includes implantable pulse generator 12, implantable lead 14, which carries an array of electrodes 18 (shown exaggerated for purposes of illustration), and optional implantable extension lead 16. Although only one lead 14 is shown, typically two or more leads are used with the therapy delivery system 10 (e.g., as shown in FIG. 1C).

Lead 14 includes elongated body 40 having proximal end 36 and distal end 44. Elongated body 40 typically has a diameter of between about 0.03 inches to 0.07 inches and a length within the range of 30 cm to 90 cm for spinal cord stimulation applications. Elongated body 40 may be composed of a suitable electrically insulative material, such as a polymer (e.g., polyurethane or silicone), and may be extruded as a unibody construction.

In the illustrated embodiment, proximal end 36 of lead 14 is electrically coupled to distal end 38 of extension lead 16 via a connector 20, typically associated with the extension lead 16. Proximal end 42 of extension lead 16 is electrically coupled to implantable pulse generator 12 via connector assembly 22 associated with housing 28. Alternatively, proximal end 36 of lead 14 can be electrically coupled directly to connector 20.

In the illustrated embodiment, implantable pulse generator 12 includes electronic subassembly 24 (shown schematically), which includes control and pulse generation circuitry (not shown) for delivering electrical stimulation energy to electrodes 18 of lead 14 in a controlled manner. Implantable pulse generator 12 of the illustrated embodiment further includes a power supply, such as battery 26.

Implantable pulse generator 12 provides a programmable stimulation signal (e.g., in the form of electrical pulses or substantially continuous-time signals) that is delivered to target stimulation sites by electrodes 18. In applications with more than one lead 14, implantable pulse generator 12 may provide the same or a different signal to electrodes 18 of the therapy delivery elements.

In accordance with some embodiments, implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In still another embodiment, implantable pulse generator 12 can take the form of an external trial stimulator (ETS), which has similar pulse generation circuitry as an implantable pulse generator (IPG), but differs in that it is a non-implantable device that is used on a trial basis after lead 14 has been implanted and prior to implantation of the IPG, to test the responsiveness of the stimulation that is to be provided.

Housing 28 is composed of a biocompatible material, such as for example titanium, and forms a hermetically sealed compartment containing electronic subassembly 24 and battery 26 is protected from the body tissue and fluids. Connector assembly 22 is disposed in a portion of housing 28 that is, at least initially, not sealed. Connector assembly 22 carries a plurality of contacts that electrically coupled with respective terminals at proximal ends of lead 14 or extension lead 16. Electrical conductors extend from connector assembly 22 and connect to electronic subassembly 24.

Figure 1B:
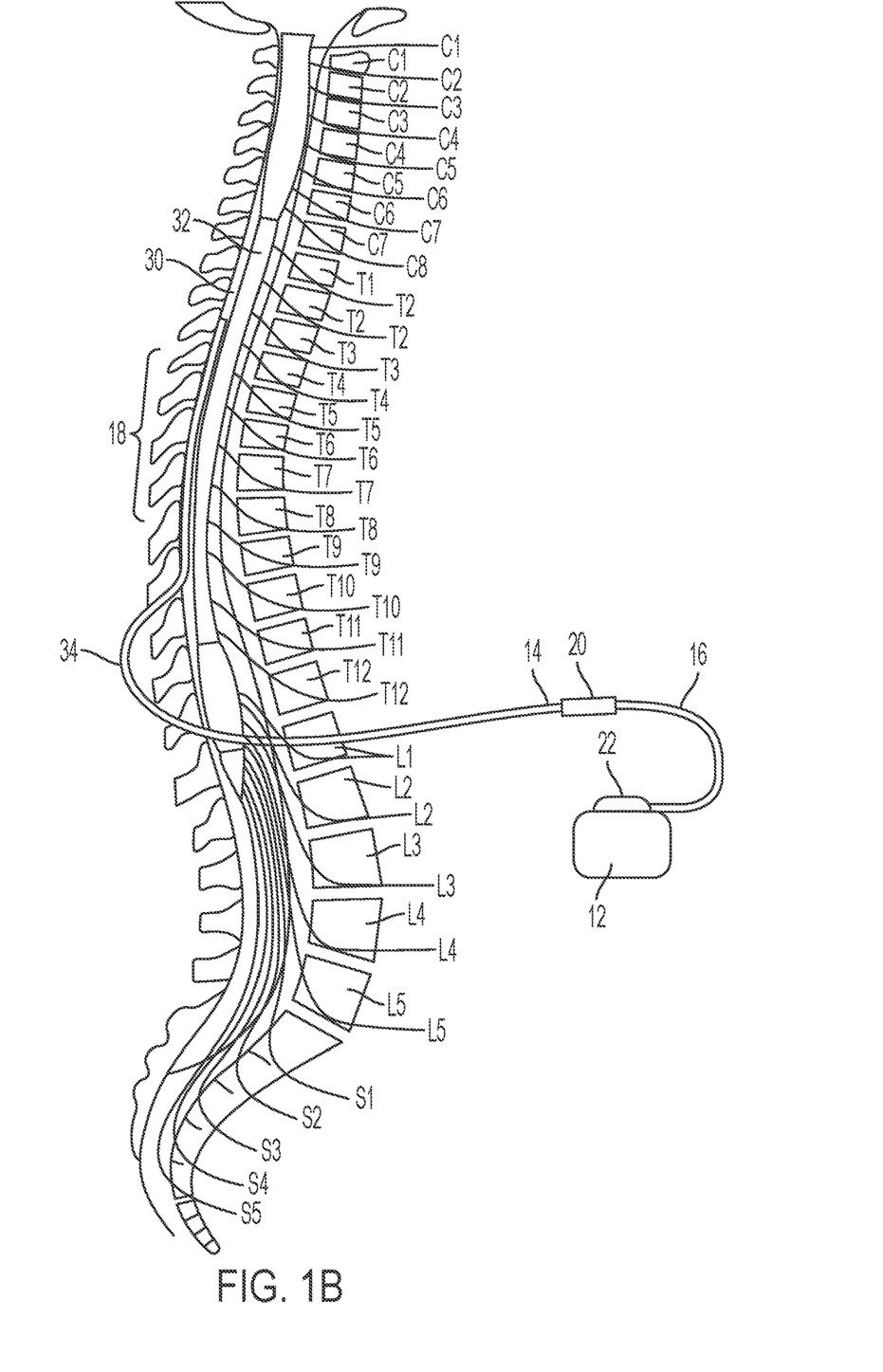
FIGS. 1B and 1C show an environment for a therapy delivery system in which a bulkhead anchor of embodiments of the present invention may be deployed.
Figure 1C:
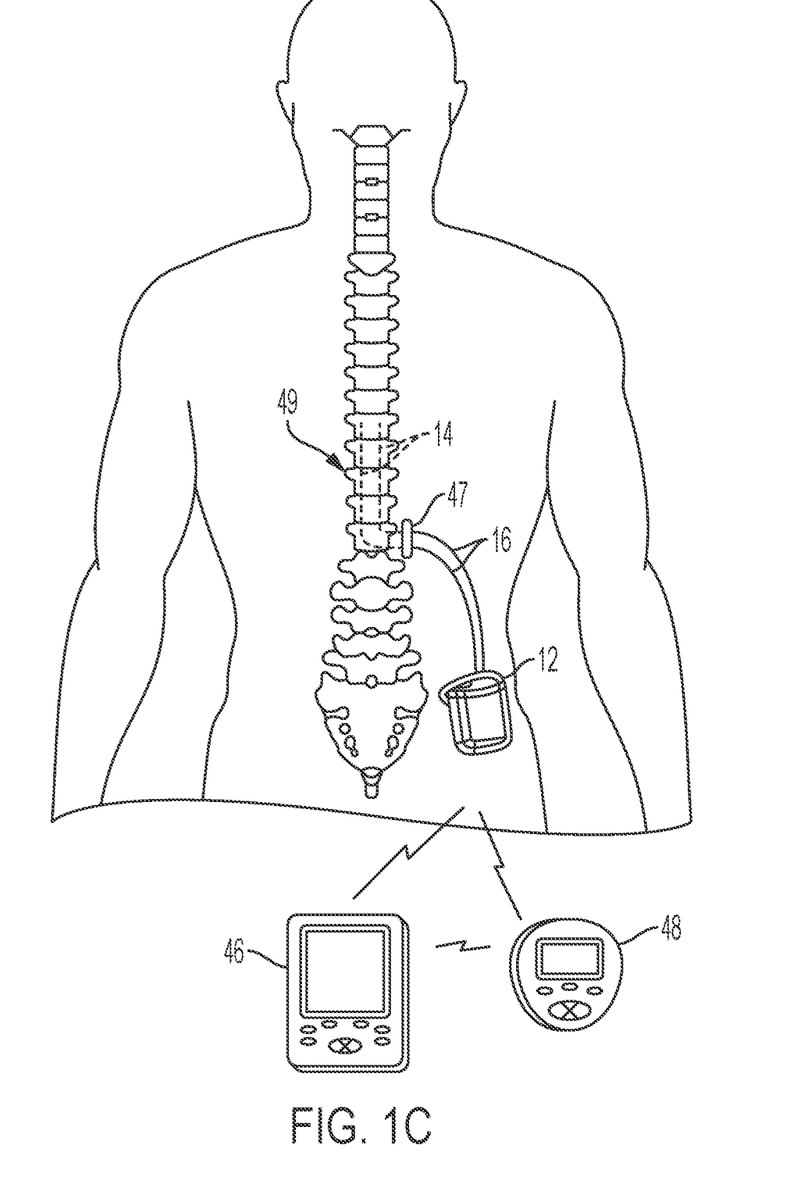

FIG. 1B illustrates lead 14 implanted in epidural space 30 of a patient in close proximity to the dura, the outer layer that surrounds spinal cord 32, to deliver the intended therapeutic effects of spinal cord electrical stimulation. The target stimulation sites may be anywhere along spinal cord 32. Such as for example proximate the sacral nerves.

Because of the lack of space near lead exit point 34 where lead 14 exits the spinal column, implantable pulse generator 12 is generally implanted in a surgically-made pocket either in the abdomen or above the buttocks, such as illustrated in FIG. 1C. Implantable pulse generator 12 may, of course, also be implanted in other locations of the patient's body. Use of extension lead 16 facilitates locating implantable pulse generator 12 away from lead exit point 34. In some embodiments, extension lead 16 serves as a lead adapter if proximal end 36 of lead 14 is not compatible with connector assembly 22 of implantable pulse generator 12, since different manufacturers use different connectors at the ends of their stimulation leads and are not always compatible with connector assembly 22.

As illustrated in FIG. 1C, therapy delivery system 10 also may include clinician programmer 46 and patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with implantable pulse generator 12 to download neurostimulation parameters and, optionally, upload operational or physiological data stored by implantable pulse generator 12. In this manner, the clinician may periodically interrogate implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and implantable pulse generator 12. Patient programmer 48 provides a patient with an interface for control of neurostimulation therapy provided by implantable pulse generator 12. For example, a patient may use patient programmer 48 to start, stop or adjust neurostimulation therapy. In particular, patient programmer 48 may permit a patient to adjust stimulation parameters such as duration, amplitude, pulse width and pulse rate, within an adjustment range specified by the clinician via clinician programmer 48, or select from a library of stored stimulation therapy programs.

Implantable pulse generator 12, clinician programmer 46, and patient programmer 48 may communicate via cables or a wireless communication. Clinician programmer 46 and patient programmer 48 may, for example, communicate via wireless communication with implantable pulse generator 12 using radio frequency (RF) telemetry techniques known in the art. Clinician programmer 46 and patient programmer 48 also may communicate with each other using any of a variety of local wireless communication techniques, such as RF communication according to the 802.11 or BLUETOOTH specification sets, infrared communication (e.g., according to the IrDA standard), or other standard or proprietary telemetry protocols.

Since implantable pulse generator 12 is located remotely from target location 49 for therapy, lead 14 and/or extension leads 16 is typically routed through a pathways subcutaneously formed along the torso of the patient to a subcutaneous pocket where implantable pulse generator 12 is located. As used hereinafter, "lead" and "lead extension" are used interchangeably, unless content clearly dictates otherwise.

Leads are typically fixed in place near the location selected by the clinician using one or more anchors 47, such as in the epidural space 30. Anchor 47 can be positioned on lead 14 in a wide variety of locations and orientations to accommodate individual anatomical differences and the preferences of the clinician. Anchor 47 may then be affixed to tissue using fasteners, such as for example, one or more sutures, staples, screws, or other fixation devices. The tissue to which anchor 47 is affixed may include subcutaneous fascia layer, bone, or some other type of tissue. Securing anchor 47 to tissue in this manner prevents or reduces the chance that lead 14 will become dislodged or will migrate in an undesired manner.

Figure 2:
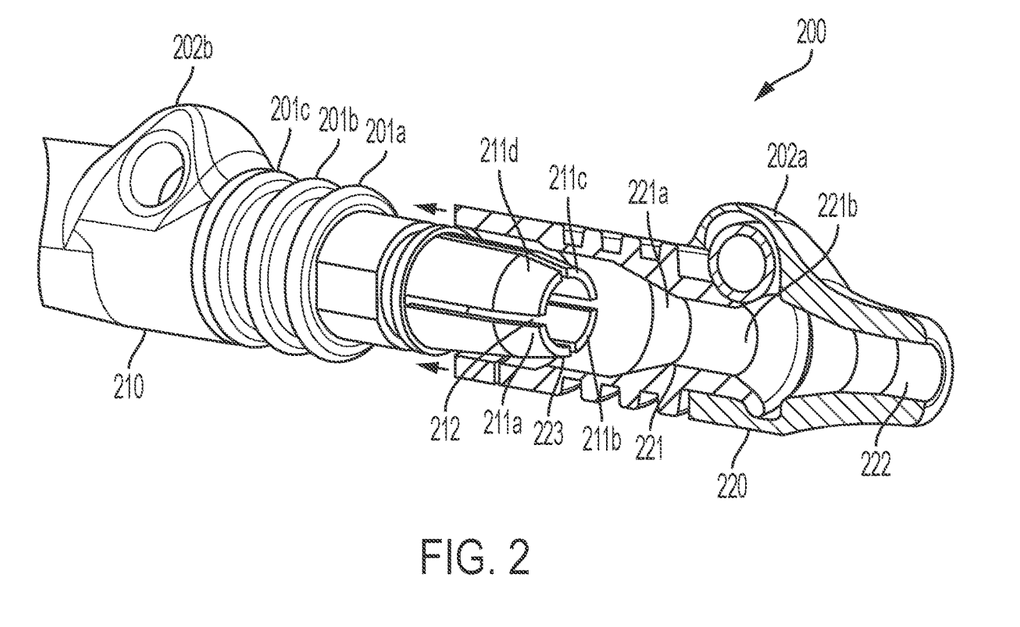
FIG. 2 shows a bulkhead anchor configuration of some embodiments of the present invention.

FIG. 2 shows an example embodiment of a bulkhead anchor configuration according to concepts of the present disclosure. Bulkhead anchor 200 shown in FIG. 2 may, for example, be utilized as anchor 47 of FIGS. 1A-1C.

Bulkhead anchor 200 of the illustrated embodiment includes flexure finger portion 210 and radial bulkhead portion 220 operable in cooperation to impart a radial compressive force to a corresponding lead body, as discussed in further detail below. It should be understood that, although the example of bulkhead anchor 200 of FIG. 2 is provided to aid in understanding the present invention, the particular embodiment illustrated is exemplary and non-limiting with respect to particular implementations encompassed by the concepts herein.

Flexure finger portion 210 of the illustrated embodiment of bulkhead anchor 200 includes a plurality of flexure finger members forming an anchor lumen configured for insertion of a lead body therein. For example, flexure finger portion 210 of the example of FIG. 2 includes flexure finger members 211a-211d disposed in a corolla (from the Latin meaning "little crown") configuration, wherein the flexure finger members are in a closed flower petal or crown-like arrangement. The corolla configuration of flexure finger members 211a-211d forms an inner diameter, shown as anchor lumen 212, through which a lead body (e.g., body of lead 14) may be inserted.

Flexure finger members 211a-211d of embodiments of the invention are configured to flex, reducing the inner diameter of the anchor lumen, and thus tighten the bulkhead anchor on a lead. For example, flexure finger members 211a-211d of embodiments may comprise rigid or substantially rigid structures, such as may be made from various forms of hard plastics, polymers, etc. (e.g., thermoplastics, such as polyethylene, polypropylene, acrylonitrile butadiene styrene (ABS), polycarbonate, etc., and/or other relatively rigid biocompatible materials) that are resistant to compression and structural deformation under operational forces. Nevertheless, the flexure finger members may be attached to the remaining structure of flexure finger portion 210 to facilitate inward deflection of at least a portion of the flexure finger members. In accordance with the illustrated example, flexure finger members 211a-211d may be comprised of individual finger members defined from material of a flexure finger body, wherein a proximal end of each flexure finger member provides a flexure joint and a distal end of each flexure finger member is substantially free (e.g., a bias of the relatively rigid material of the flexure finger member to remain in its resting orientation is overcome) to move inward (e.g., towards a center of anchor lumen 212) to at least some extent.

The size, shape, thickness, rigidity, etc. of flexure finger members 211a-211d may be selected to accommodate flexure and finger member movement as described herein. For example, the thickness profile of at least a portion of the finger members (e.g., providing a thinner material profile at a flexure joint portion of each flexure finger) may be configured to accommodate flexure of the flexure fingers sufficient to accommodate inward movement for gripping a lead body. In accordance with embodiments of the invention, the finger members may be sized and shaped (e.g., provided with a sufficient gap between fingers and a distal end shape of each finger) to provide sufficient clearance between the flexure fingers to accommodate their inward movement to a position that an inner diameter, and thus a diameter of anchor lumen 212, is sized for gripping a lead. The flexure finger members of embodiments may additionally or alternatively comprise one or more features for aiding in gripping of the lead (e.g., features provided upon a portion of the flexure fingers contacting a lead body disposed in the anchor lumen), such as having surface perturbations (e.g., ribs, "saw tooth" surface features, abrasive surface features, etc.), over-molded in a material (e.g., polyurethane or silicone) that increases the friction between lead and anchor and/or facilitates uniform or improved distribution of gripping forces over a surface area of the lead body (e.g., avoiding or minimizing damage to the lead associated with sharp or shear forces while increasing a grip on the lead), etc. One or more features of the flexure finger members may additionally or alternatively be configured for distributing compressive forces over the surface of a lead, such as to take up any inconsistencies, perturbations, or features in or on the surface of the lead. For example, a resilient material of a material over-molded on one or more of the flexure fingers may conform to features (e.g., irregularities, detents, burrs, etc.) on the lead surface to facilitate an excellent gripping interface between the flexure finger portion and the lead.

Radial bulkhead portion 220 of the illustrated embodiment of bulkhead anchor 200 includes a radial bulkhead configured to operatively engage the plurality of flexure finger members of flexure finger portion 210 for affixing bulkhead anchor 200 to a lead. In the illustrated example, radial bulkhead portion 220 of the example of FIG. 2 includes radial bulkhead 221 defined within an interior area of the radial bulkhead portion facing inward. For example, radial bulkhead 221 of embodiments may be disposed within a transition area of radial bulkhead portion 220 between anchor lumen 222 and flexure finger portion lumen 223, whereby radial bulkhead portion 220 may be interfaced with flexure finger portion 210 and at least a portion of flexure finger members 211a-211d engaged by radial bulkhead 221.

Radial bulkheads of embodiments of the invention comprise a flexure profile configured to operatively engage a plurality of flexure finger members and induce flexure of the flexure finger members in accordance with concepts herein. The example illustrated in FIG. 2 provides a configuration in which the flexure profile of radial bulkhead 221 defines an area of reduced inner diameter (e.g., annular engagement surface 221a) as compared to flexure finger portion lumen 223. Such an area of reduced inner diameter may be configured to operatively engage the flexure finger members and causing their inward displacement. For example, annular engagement surface 221a of embodiments may provide an annular flexure point of radial bulkhead portion 220 configured to interface with the flexure finger members of flexure finger portion 210 and induce the flexure of the flexure finger members. The flexure profile of radial bulkhead 221 in the example of FIG. 2 further includes a sloping surface (e.g., annular sloping surface 221b) configured to interface with the plurality of flexure finger members and progressively induce the flexure of the flexure finger members and encourage the radial compressive force (e.g., facilitate a smooth transition from resting orientation of the flexure finger members to their full inward deflected orientation provided by their engaging annular engagement surface 221a).

Flexure profiles implemented according to some embodiments of the invention may be configured to provide one or more desired attributes with respect to a transition from resting orientation of the flexure finger members to their full inward deflected orientation. For example, a flexure profile may comprise a multi-gradient sloping surface (e.g., a surface presenting a first portion having a first slope gradient, a second portion having a second slope gradient, and so on) configured to provide a desired or otherwise predetermined force displacement profile. The multi-gradient sloping surface of the embodiment of the flexure profile illustrated in FIG. 2, for example, provides a greater slope with respect to a portion (e.g., annular engagement surface 221a) of the flexure profile that initially interfaces with the flexure fingers and a lesser slope with respect to a portion (e.g., annular sloping surface 221b) of the flexure profile that interfaces with the flexure fingers as they reach their full inward deflected orientation. The force displacement profile of the foregoing flexure profile may, for example, offset differences with respect to the force used to move the flexure fingers to their engaged position throughout the transition, such as due to lower resistance (and thus less force needed to move the flexure fingers inward) at initiation of the flexure when the flexure fingers do not experience any or much resistance from the lead (e.g., taking up a gap between the flexure fingers and the lead) and greater resistance (and thus more force needed to continue movement of the flexure fingers inward to their engaged position) at or near completion of the flexure when the flexure fingers are firmly engaged with the lead. Annular sloping surface 221b of embodiments may itself present multiple gradients configured to tune the force displacement profile of a particular bulkhead anchor implementation. Bulkhead anchors of embodiments may be engaged through manual manipulation, whereby a flexure profile configuration (e.g., a multi-gradient sloping surface configuration) according to some aspects of the disclosure may provide a constant (or other desired attribute) tactile feedback to a clinician engaging the anchor.

Although the example of FIG. 2 has been described above with reference to radial bulkhead 221 comprising a flexure profile, it should be understood that flexure finger members of embodiments of the invention may additionally or alternatively comprise a flexure profile. For example, outer surfaces (e.g., an area of the flexure finger members facing outward) of flexure finger members 211a-211d of embodiments may comprise a topology providing an annular flexure point configured to interface with a radial bulkhead of radial bulkhead portion 220 and induce the flexure of the flexure finger members.

In operation according to embodiments, as radial bulkhead portion 220 of bulkhead anchor 200 is moved toward flexure finger portion 210 (e.g., moved in the direction of the arrows shown in FIG. 2), radial bulkhead 221 engages the distal end of flexure finger members 211a-211d and encourages their inward deflection. For example, annular sloping surface 221b of the flexure profile provided by the radial bulkhead may engage the flexure finger members and initiate their inward deflection. Thereafter, as radial bulkhead portion 220 is continued to be moved toward flexure finger portion 210, annual engagement surface 221a may engage the flexure finger members and encourage a radial compressive force to be imparted upon the lead body inserted in anchor lumen 212 (e.g., when radial bulkhead portion 220 is disposed in an engaged position with respect to flexure finger portion 210). Accordingly, once bulkhead anchor 200 is disposed at a desired position axially along a lead body, radial bulkhead portion 220 may be manipulated to interface with flexure finger portion 210, induce flexure of the flexure finger members, causing a radial compressive force to be imparted upon the lead body and thereby affixing or "locking" the bulkhead anchor on the lead. That is, flexure finger members 211a-211d of bulkhead anchor 200 are pushed into the lead, clamping it evenly around its circumference. The interaction between radial bulkhead portion 220 and flexure finger portion 210 of embodiments distributes the clamping force evenly (e.g., the flexure finger members relatively uniformly squeeze the lead around a portion at which the anchor is disposed) around a large length of the lead, providing a suitably high pull-out force while reducing the local maximum lead stress which minimizes lead damage.

Aspects of various parameters may be selected to adjust or otherwise control an amount of radial compressive force exerted and how that force is distributed upon a lead by a bulkhead anchor of embodiments. For example, the number of flexure finger members used, the contact length and/or width between the flexure finger members and the lead, and the compression between the flexure finger members and the lead are examples of parameters for which aspects may be selected in order to provide a desired amount of pull out force with respect to a lead disposed in an affixed or "locked" bulkhead anchor. In accordance with embodiments of the invention, the inner diameter of annular engagement surface 221a, the axial length of annular engagement surface 221a, the number of flexure finger members 211a-211d, and the radial thickness of flexure finger members 211a-211d may, for example, be selected to adjust or control radial compressive forces applied to a lead by bulkhead anchor 200. The number of flexure finger members used, the contact length and/or width between the flexure finger members and the lead, the shape of the surface of the flexure fingers contacting the lead, the surface configuration of the flexure fingers (e.g., over-molded with a soft elastomeric material, contoured to the size and shape of the lead, etc.), and the morphology of the flexure fingers (e.g., precisely how the flexure fingers move, deform, flex, etc. in transitioning to an engaged position) are examples of parameters for which aspects may be selected in order to provide a desired distribution of compressive forces over the surface of a lead disposed in an affixed or "locked" bulkhead anchor. Using such techniques, bulkhead anchors according to concepts of the present invention may be configured to provide a tight friction interface between the anchor and the lead without introducing sharp concentrated shear forces on the lead that can be stress points.

One or more locking mechanisms may be used to retain the flexure finger portion and the radial bulkhead portion of a bulkhead anchor in their relative positions with respect to each other such that a radial compressive force is maintained upon the lead body indefinitely (e.g., until the locking mechanism is disengaged or otherwise released). For example, flexure finger portion 210 or radial bulkhead portion 220 may include a ring or rib structure while the other one of radial bulkhead portion 220 or flexure finger portion 210 may include a corresponding groove configured to cooperatively operate as a locking mechanism. In accordance with some examples, when radial bulkhead portion 220 is fully interfaced with flexure finger portion 210 (e.g., the flexure finger members are displaced inwardly and a desired radial compressive force is imparted upon the lead body), the aforementioned ring and groove may align such that the ring engages the groove and discourages relative movement (e.g., separation) of flexure finger portion 210 and radial bulkhead portion 220 (e.g., until sufficient force is applied to overcome the ring and groove engagement).

Figure 3A:
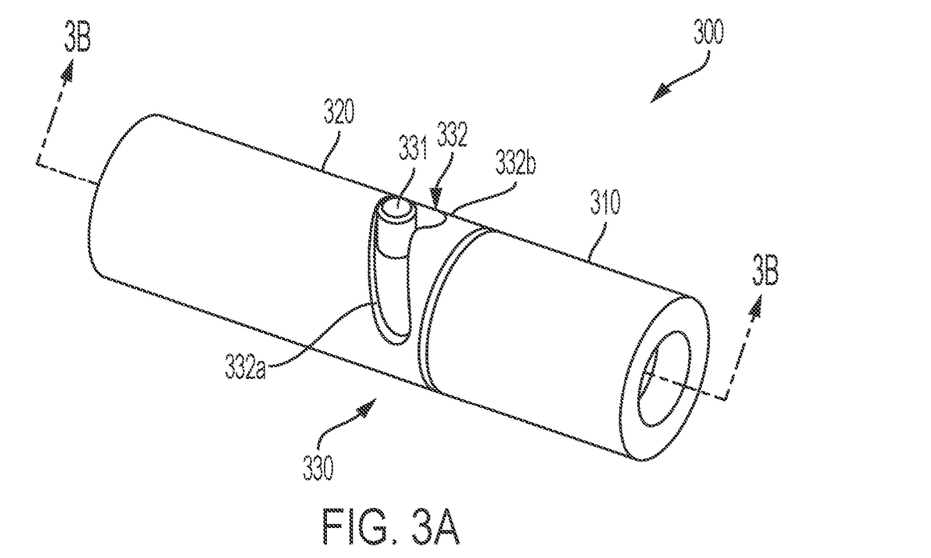
FIGS. 3A and 3B show a bulkhead anchor configuration of some additional embodiments of the present invention.
Figure 3B:
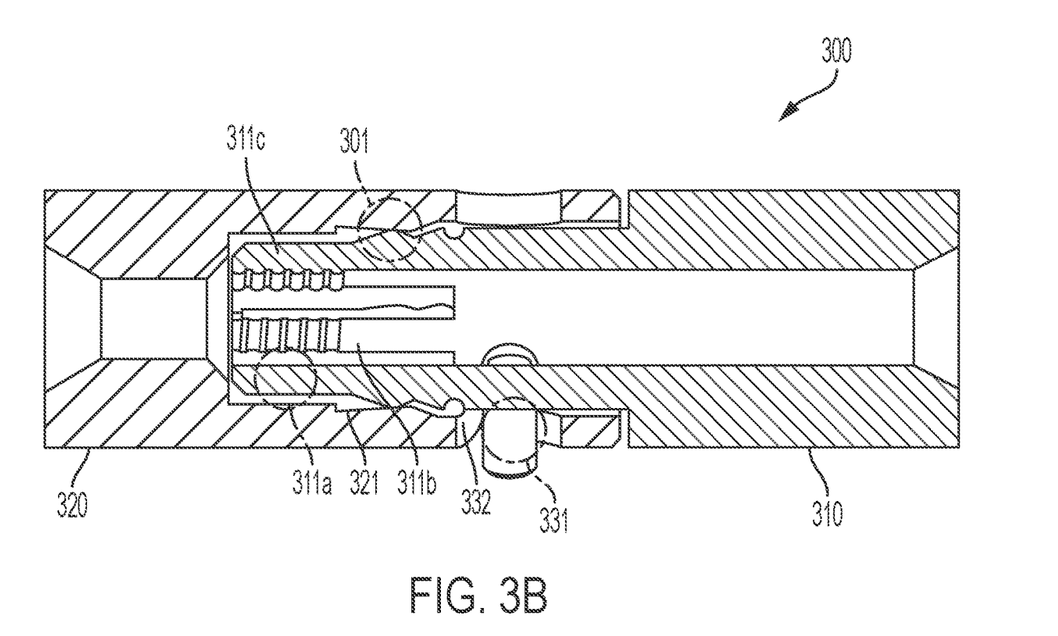

FIGS. 3A and 3B show an example embodiment of a bulkhead anchor configuration comprising a locking mechanism according to concepts of the present disclosure. Similar to bulkhead anchor 200 of FIG. 2, bulkhead anchor 300 shown in FIG. 3 includes a flexure finger portion (shown as flexure finger portion 310) and a radial bulkhead portion (shown as radial bulkhead portion 320), such as may be utilized as anchor 47 of FIGS. 1A-1C. It should be understood that, although the example of bulkhead anchor 300 of FIG. 3. is provided to aid in understanding the present invention, the particular embodiment illustrated is exemplary and non-limiting with respect to particular implementations encompassed by the concepts herein.

Flexure finger portion 310 and radial bulkhead portion 320 of bulkhead anchor 300 are operable in cooperation to impart a radial compressive force to a corresponding lead body. Accordingly, radial bulkhead 321 is defined within an interior area of radial bulkhead portion 320 to engage the flexure finger members (flexure finger members 311a-311c being visible in the cross section view of FIG. 3B), and encourage their inward displacement. For example, as radial bulkhead portion 320 of bulkhead anchor 300 is moved toward flexure finger portion 310, radial bulkhead 321 engages the distal end of flexure finger members 311a-311c (additional flexure finger members not being visible in the illustrations of FIGS. 3A and 3B) and encourages their inward deflection. As radial bulkhead 321 fully engages the flexure finger members (e.g., such as the flexure profile of the radial bulkhead coming into juxtaposition with a corresponding feature of a flexure provide of a flexure profile of the flexure finger members, such as at annular flexure point 301) a portion of a lead body disposed within the anchor lumen may be gripped by imparting a radial compressive force to the lead body. In operation according to bulkhead anchor 300 of the example of FIGS. 3A and 3B, the radial compressive force is maintained upon the lead body by operation of locking mechanism 330 configured to retain flexure finger portion 310 and radial bulkhead portion 320 in their relative positions.

Locking mechanism 330 of the example shown in FIGS. 3A and 3B provides a bayonet-type mechanism in which twisting action may be employed to engage a pin to retain the relative positions of flexure finger portion 310 and radial bulkhead portion 320. Accordingly, locking mechanism 330 of the illustrated embodiment includes pin 331 disposed in slot 332. Pin 331 and slot 332 are each part of or affixed to a different one of flexure finger portion 310 and radial bulkhead portion 320 of bulkhead anchor 300. For example, pin 331 of the example shown is affixed to flexure finger portion 310, whereas slot 332 is shown in the example to be provided within an area of radial bulkhead portion 320 receiving flexure finger portion 310.

Slot 320 is shaped to provide a sloping slot section (shown as slot section 332a) facilitating axial movement of radial bulkhead portion 320 with respect to flexure finger portion 310. Accordingly, as pin 331 travels through slot section 332a (e.g., as flexure finger portion 310 and radial bulkhead portion 320 are pressed axially together and a radial twisting motion is provided to one of flexure finger portion 310 or radial bulkhead portion 320) relative movement of radial bulkhead portion 320 is provided to engage the flexure finger members for affixing or "locking" the bulkhead anchor on a lead). Slot 320 is further shaped to provide a locking detent section (shown as slot section 332b) facilitating engaging pin 331 for retaining flexure finger portion 310 and radial bulkhead portion 320 in their engaged configuration. Accordingly, as pin 331 enters into slot section 332b (e.g., as flexure finger portion 310 and radial bulkhead portion 320 are pressed together axially sufficiently to have fully engaged and the extent of radial twisting motion accommodated by locking mechanism has completed) relative movement of radial bulkhead portion 320 may be discouraged due to pin 331 resting within the detent of slot section 332b. As can be appreciated from the foregoing, the bayonet-type mechanism of locking mechanism 330 provides for operation in which a 90° twist secures bulkhead anchor 300 into its locked position without the use of tools. To unlock, flexure finger portion 310 and radial bulkhead portion 320 may be pushed toward each other and twisted in the opposite direction to release locking mechanism 330.

It should be appreciated that bulkhead anchors provided in accordance with concepts of the present invention may include one or more structures providing additional or alternative functionality to that of exemplary embodiments described above. For example, in addition to being configured to engage a lead body so as to maintain a relative position axially with respect to the lead, bulkhead anchors of embodiments of the invention may be configured for affixing to surrounding tissue of a patient within which the lead is disposed. Bulkhead anchors 200 and 300 may, for example, be affixed to tissue using various forms of fasteners (e.g., sutures, staples, screws, and/or other fixation devices). Accordingly, flexure finger portions and/or radial bulkhead portions of embodiments of the invention may comprise one or more structures to assist affixing of the bulkhead anchor to tissue of the patient. For example, one or more rib structures, such as ribs 201a-201c shown on flexure finger portion 210 in FIG. 2, may be provided for use in affixing the bulkhead anchor to tissue. Additionally or alternatively, one or more anchor loops, such as anchor loops 202a and 202b shown on flexure finger portion 210 and radial bulkhead portion 220 in FIG. 2, or other similar structures may be provided on a bulkhead anchor of embodiments.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. An anchor for a medical device lead, the anchor comprising:
    a flexure finger portion having a plurality of flexure finger members forming an anchor lumen configured for insertion of a lead body therein;
    a radial bulkhead portion having a radial bulkhead with a flexure profile configured to operatively engage the plurality of flexure finger members and induce flexure of the flexure finger members, wherein the flexure profile of the radial bulkhead is configured to encourage radial compressive forces to be imparted upon the lead body inserted in the anchor lumen when the radial bulkhead portion is disposed in an engaged position with respect to the flexure finger portion, and wherein the flexure profile comprises a multi-gradient sloping surface configured to provide a predetermined force displacement profile with respect to movement of the plurality of flexure finger members from a disengaged position through an engaged position in which the flexure of the flexure finger members is induced and the radial compressive forces are encouraged; and
    a locking mechanism configured to retain the flexure finger portion and the radial bulkhead portion in relative positions to maintain the flexure of the flexure finger members.

2. The anchor of claim 1, wherein the plurality of flexure finger members each have a flexure profile configured to cooperate with the flexure profile of the radial bulkhead portion and induce flexure of the flexure finger members to encourage the radial compressive forces.

3. The anchor of claim 1, wherein the flexure profile comprises an annular flexure point configured to interface with the plurality of flexure finger members and induce the flexure of the flexure finger members and encourage the radial compressive forces.

4. The anchor of claim 1, wherein the radial compressive forces are distributed substantially equally around the lead body.

5. The anchor of claim 1, wherein the radial compressive force ii forces are maintained upon the lead body during operation of the locking mechanism retaining the flexure finger portion and the radial bulkhead portion in the relative positions.

6. The anchor of claim 1 wherein the plurality of flexure finger members are disposed in a corolla configuration around the anchor lumen.

7. The anchor of claim 1, wherein one or more individual flexure finger members of the plurality of flexure finger members comprise one or more features configured for aiding in gripping of the lead body.

8. The anchor of claim 7, wherein the one or more features configured for aiding in gripping of the lead body comprise surface perturbations.

9. The anchor of claim 7, wherein the one or more features configured for aiding in gripping of the lead body comprises a material over-molded on the one or more individual flexure finger members.

10. The anchor of claim 1, wherein one or more individual flexure finger members of the plurality of flexure finger members comprise one or more features configured for aiding in distributing the radial compressive forces over a surface of the lead body.

11. The anchor of claim 10, wherein the one or more features configured for aiding in distributing the radial compressive forces over the surface of the lead body comprise a morphology of the plurality of flexure finger members.

12. The anchor of claim 10, wherein the one or more features configured for aiding in distributing the radial compressive forces over the surface of the lead body comprises a material over-molded on the one or more individual flexure finger members.

13. The anchor of claim 1, wherein the locking mechanism comprises a bayonet interface configured to retain the flexure finger portion and the radial bulkhead portion in the relative positions.

14. The anchor of claim 1, wherein the locking mechanism comprises an annular ring and groove interface configured to retain the flexure finger portion and the radial bulkhead portion in the relative positions.

15. The anchor of claim 1, wherein the medical device lead comprises an electrical lead for an implantable medical device.

16. The anchor of claim 1, wherein the medical device lead comprises a catheter for an implantable medical device.

17. The anchor of claim 1, further comprising:
    one or more tissue anchor members configured for affixing the anchor to adjacent tissue of a body into which the medical device lead is implanted.

18. The anchor of claim 1, wherein the flexure profile is configured to offset differences with respect to a force used to move the plurality of flexure finger members from the disengaged position to the engaged position.

19. The anchor of claim 18, wherein the flexure profile is configured to provide a constant tactile feedback to a clinician engaging the anchor.

20. A method for affixing an anchor to a medical device lead, the method comprising:
    manipulating a radial bulkhead portion of the anchor with respect to a flexure finger portion of the anchor, wherein a plurality of flexure finger members of the flexure finger portion form an anchor lumen configured for insertion of a lead body therein and a flexure profile of a radial bulkhead of the radial bulkhead portion operatively engages the plurality of flexure finger members and induces flexure of the flexure finger members in response to the manipulating, wherein the flexure profile of the radial bulkhead is configured to encourage radial compressive forces to be imparted upon the lead body inserted in the anchor lumen when the radial bulkhead portion is disposed in an engaged position with respect to the flexure finger portion, and wherein the flexure profile comprises a multi-gradient sloping surface configured to provide a predetermined force displacement profile with respect to movement of the plurality of flexure finger members from a disengaged position through an engaged position in which the flexure of the flexure finger members is induced and the radial compressive forces are encouraged; and engaging a locking mechanism configured to retain the flexure finger portion and the radial bulkhead portion in relative positions to maintain the flexure of the flexure finger members.

21. The method of claim 20, wherein the flexure profile comprises an annular flexure point configured to interface with the plurality of flexure finger members and induce the flexure of the flexure finger members and encourage the radial compressive forces.

22. The method of claim 20, wherein the radial compressive forces are distributed substantially equally around the lead body.

23. The method of claim 20 wherein the radial compressive forces are maintained upon the lead body during operation of the locking mechanism retaining the flexure finger portion and the radial bulkhead portion in the relative positions.

24. The method of claim 20, wherein the plurality of flexure finger members are disposed in a corolla configuration around the anchor lumen.

25. The method of claim 20, wherein one or more individual flexure finger members of the plurality of flexure finger members comprise one or more features configured for aiding in gripping of the lead body.

26. The method of claim 20, wherein one or more individual flexure finger members of the plurality of flexure finger members comprise one or more features configured for aiding in distributing the radial compressive forces over a surface of the lead body.

27. The method of claim 20, wherein the engaging the locking mechanism comprises:

engaging a bayonet interface configured to retain the flexure finger portion and the radial bulkhead portion in the relative positions.

28. The method of claim 20, wherein the engaging the locking mechanism comprises:

engaging an annular ring in a corresponding groove configured to retain the flexure finger portion and the radial bulkhead portion in the relative positions.

29. The method of claim 20, wherein the medical device lead comprises an electrical lead for an implantable medical device.

30. The method of claim 20, wherein the medical device lead comprises a catheter for an implantable medical device.

31. The method of claim 20, further comprising:

affixing the anchor to adjacent tissue of a body into which the medical device lead is implanted using one or more tissue anchor members of the anchor.

32. The method of claim 20, wherein the flexure profile is configured to offset differences with respect to a force used to move the plurality of flexure finger members from the disengaged position to the engaged position.

33. The method of claim 32, wherein the flexure profile is configured to provide a constant tactile feedback to a clinician engaging the anchor.

34. An anchor for a medical device lead, the anchor comprising:

a flexure finger portion having a plurality of flexure finger members forming an anchor lumen configured for insertion of a lead body therein, wherein the plurality of flexure finger members are disposed in a corolla configuration around the anchor lumen;

a radial bulkhead portion having a radial bulkhead with a flexure profile configured to operatively engage the plurality of flexure finger members and induce flexure of the flexure finger members, wherein the flexure profile of the radial bulkhead is configured to encourage a radial compressive forces to be substantially equally imparted around a portion of the lead body inserted in the anchor lumen when the radial bulkhead portion is disposed in an engaged position with respect to the flexure finger portion, and wherein the flexure profile comprises a multi-gradient sloping surface configured to provide a predetermined force displacement profile with respect to movement of the plurality of flexure finger members from a disengaged position through an engaged position in which the flexure of the flexure finger members is induced and the radial compressive forces are encouraged;

a locking mechanism configured to retain the flexure finger portion and the radial bulkhead portion in relative positions to maintain the flexure of the flexure finger members, wherein the radial compressive forces are maintained upon the lead body during operation of the locking mechanism retaining the flexure finger portion and the radial bulkhead portion in the relative positions; and one or more tissue anchor members configured for affixing the anchor to adjacent tissue of a body into which the medical device lead is implanted.

35. The anchor of claim 34, wherein the flexure profile comprises an annular flexure point configured to interface with the plurality of flexure finger members and induce the flexure of the flexure finger members and encourage the radial compressive forces.

36. The anchor of claim 34, wherein one or more individual flexure finger members of the plurality of flexure finger members comprise one or more features configured for aiding in gripping of the lead body.

37. The anchor of claim 34, wherein one or more individual flexure finger members of the plurality of flexure finger members comprise one or more features configured for aiding in distributing the radial compressive forces over a surface of the lead body.

38. The anchor of claim 34, wherein the locking mechanism comprises a bayonet interface configured to retain the flexure finger portion and the radial bulkhead portion in the relative positions.

39. The anchor of claim 34, wherein the locking mechanism comprises an annular ring and groove interface configured to retain the flexure finger portion and the radial bulkhead portion in the relative positions.

40. The anchor of claim 34, wherein the flexure profile is configured to offset differences with respect to a force used to move the plurality of flexure finger members from the disengaged position to the engaged position.

* * * * *

UNITED STATES PATENT AND TRADEMARK OFFICE
CERTIFICATE OF CORRECTION

PATENT NO. : 11,833,359 B2
APPLICATION NO. : 17/228238
DATED : December 5, 2023
INVENTOR(S) : Chris Dawson et al.

It is certified that error appears in the above-identified patent and that said Letters Patent is hereby corrected as shown below:

In the Specification

At Column 2, Line number 59, delete "(Mill)" and replace with --(MRI)--.

In the Claims

At Column 13, Claim number 5, Line number 59, delete "force ii forces are maintained" and replace with --forces are maintained--.
At Column 13, Claim number 6, Line number 63, delete "claim 1" and replace with --claim 1,--.
At Column 15, Claim number 23, Line number 17, delete "claim 20" and replace with --claim 20,--.

Signed and Sealed this
Thirtieth Day of January, 2024

Katherine Kelly Vidal
*Director of the United States Patent and Trademark Office*